US006632398B1

(12) United States Patent
Nebuloni et al.

(10) Patent No.: US 6,632,398 B1
(45) Date of Patent: Oct. 14, 2003

(54) ROTOR FOR PRESENTING SAMPLES IN PHOTOMETRIC ANALYSIS

(75) Inventors: Luigi Nebuloni, Ossona (IT); Elena Lattuada, Paderno D. (IT)

(73) Assignee: Instrumentation Laboratory, S.p.A., Milan (IT)

( * ) Notice: Subject to any disclaimer, the term of this patent is extended or adjusted under 35 U.S.C. 154(b) by 0 days.

(21) Appl. No.: 09/553,277

(22) Filed: Apr. 20, 2000

(30) Foreign Application Priority Data

Apr. 20, 1999 (EP) .............................. 99830228

(51) Int. Cl.[7] .............................................. G01N 35/00
(52) U.S. Cl. ............................................. 422/64; 436/45
(58) Field of Search .......................... 436/45; 422/64, 422/67, 102; 356/246, 440

(56) References Cited

U.S. PATENT DOCUMENTS

| 4,580,896 A | | 4/1986 | Brickus et al. | 356/246 |
|---|---|---|---|---|
| 4,580,897 A | * | 4/1986 | Nelson et al. | 356/246 |
| 4,652,137 A | | 3/1987 | Calzi | 356/427 |
| 4,680,164 A | | 7/1987 | Kelln | 422/72 |
| 4,726,683 A | | 2/1988 | Nebuloni | 356/427 |
| 4,902,479 A | | 2/1990 | Brickus | 422/72 |
| 5,071,625 A | * | 12/1991 | Kelln et al. | 422/72 |
| 5,256,376 A | * | 10/1993 | Callan et al. | 356/246 |
| 5,266,268 A | | 11/1993 | Antocci et al. | 422/72 |

FOREIGN PATENT DOCUMENTS

| EP | 0123178 | 10/1984 |
|---|---|---|
| EP | 0163038 | 12/1985 |
| EP | 0193016 | 9/1986 |
| EP | 0195893 | 10/1986 |
| EP | 1046916 | 10/2000 |

* cited by examiner

Primary Examiner—Jeffrey Snay
(74) Attorney, Agent, or Firm—Testa, Hurwitz & Thibeault, LLP

(57) ABSTRACT

The present invention relates to photometric analysis apparatus of the type which uses disk-shaped rotors, in which the rotors are loaded automatically. In particular, the present invention relates to photometric analysis apparatus of the type which uses disk-shaped rotors, characterized in that it has a device for loading the rotors (3) onto analysis apparatus (5) automatically, the device comprising a hopper (2) for supplying the rotors, the hopper (2) comprising asymmetric notches for locating the rotors (3) positively in the hopper.

8 Claims, 6 Drawing Sheets

ROTOR FOR PRESENTING SAMPLES IN PHOTOMETRIC ANALYSIS

The present invention relates to photometric analysis apparatus of the type which uses disk-shaped rotors, in which the rotors are loaded automatically.

Photometric analysis apparatus using disk-shaped rotors is widely known. The disk-shaped rotors, which are generally made of plastics material, comprise a plurality of cuvettes arranged radially around a central hole. The cuvettes provide a plurality of communicating chambers separated by partitions. The rotor is connected to a hub connected to a motor which imparts rotary motion to the rotor. A sample to be analyzed and the appropriate reagents are introduced into each cuvette. The reagents are mixed by centrifugal effect when the rotor reaches a predetermined speed of rotation. In the next step, the individual cuvettes are brought sequentially into alignment with optical analysis means by programmed rotation of the rotor.

The general structure of the rotors and of the photometric analysis apparatus is known per se and will therefore not be described in greater detail herein. The function of the rotors and the way in which they interact with the sensors for analyzing the samples are described, for example, in the Applicant's Italian patent application No. 20560A/83.

This photometric analysis apparatus is arranged to perform a large number of analyses in sequence. Clearly therefore, an essential characteristic of these machines is speed of operation. However, speed of operation must be combined with considerable precision in the execution of all of the steps of the analysis process from the loading of the rotors to their positioning on the hub, and to the perfect alignment of the cuvettes with the optical analysis means. A perfect and repeatable relationship between the positions of the cuvette and of the photoanalysis means is in fact essential for the reliability of the measurement.

The problem upon which the present invention is based is that of providing analysis apparatus having an automatic rotor-loading system which permits fast and accurate operation.

This problem is solved by photometric analysis apparatus and by a rotor as claimed in the appended claims.

Further characteristics and advantages of the photometric analysis apparatus of the present invention will become clearer from the description of an embodiment thereof given by way of non-limiting example below with reference to the following drawings.

Figure 1:
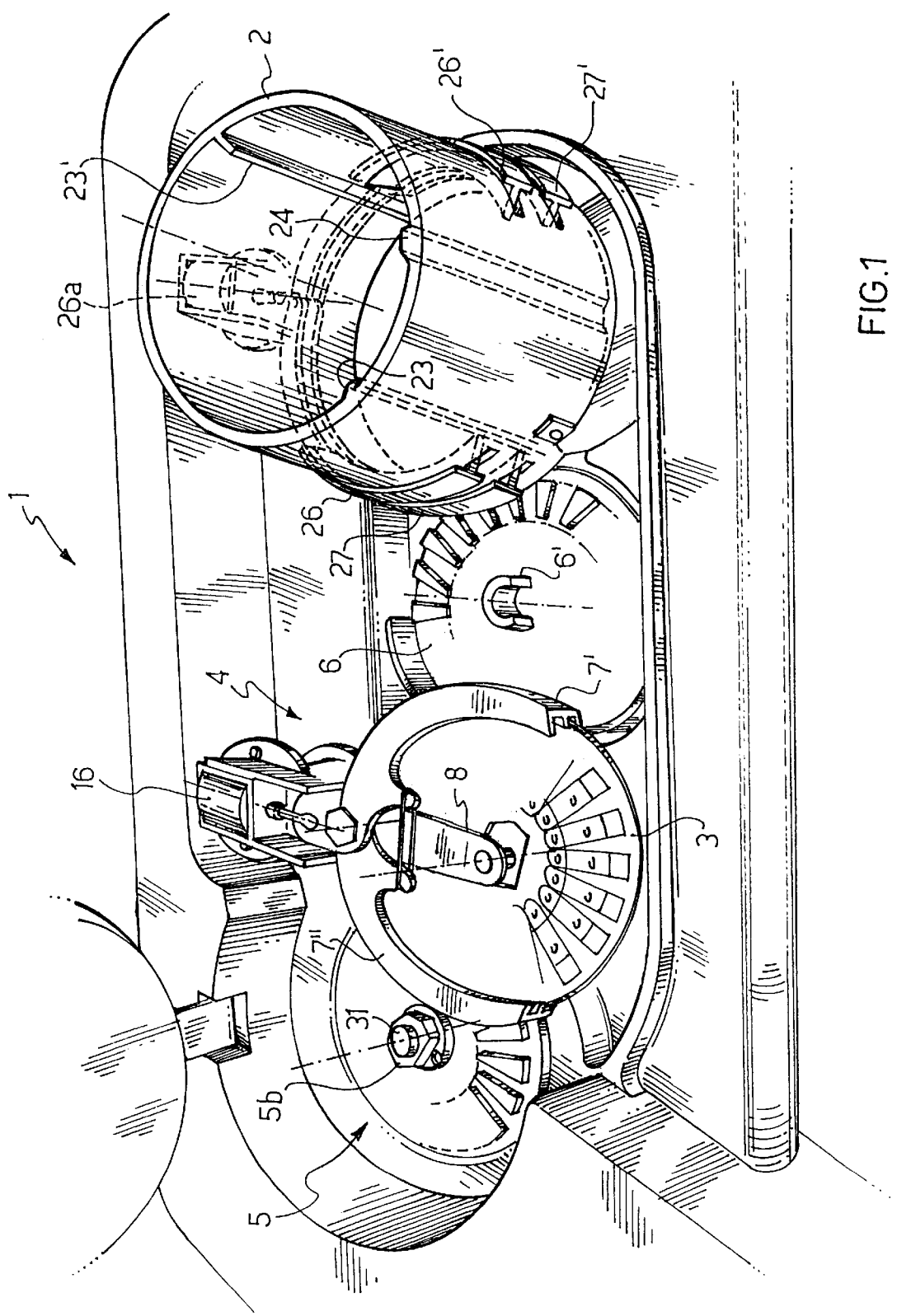
FIG. 1 is a partially-sectioned, perspective view of the photometric analysis apparatus of the present invention.

With reference to the above-mentioned drawings, the photometric analysis apparatus of the present invention is generally indicated 1. The apparatus comprises a hopper 2 for the loading of the rotors 3, and a pincer 4 for automatically transferring the rotors from a pick-up position beside the hopper 2 to the analysis unit 5, in the region of the optical analysis means (not shown in the drawings). The analysis unit 5 comprises means for imparting rotary motion to the rotor 3, and optical analysis means. The means for rotating the rotor comprise an electric motor connected to a transmission shaft 5a, to the upper end of which a hub 5b is fixed. The rotor 3 is positioned on the hub. It is extremely important to ensure the correct angular positioning of the rotor 3 on the hub so as to achieve perfect alignment of the cuvettes with the optical analysis means. The analysis unit 5, however, is of a type the general structure of which is widely known.

The apparatus 1 also comprises a plate 6 supported for sliding on the apparatus beneath the hopper 2. The plate 6 is moved by an electric actuator and can adopt a first position beneath the hopper 2 and in alignment with the longitudinal axis thereof, and a second position beneath the pick-up position of the pincer 4.

The plate 6 is circular and has dimensions substantially corresponding to those of the rotor 3. The plate 6 also has raised edges and, centrally, a pin 6' to be housed in the central hole of the rotor 3. Triangular raised portions formed on the surface of the plate 6 are arranged radially around the pin 6'. These triangular raised portions are intended to engage in the angular spaces formed between one cuvette and another on the lower surface of the rotor 3 (see FIG. 4).

Figure 2:
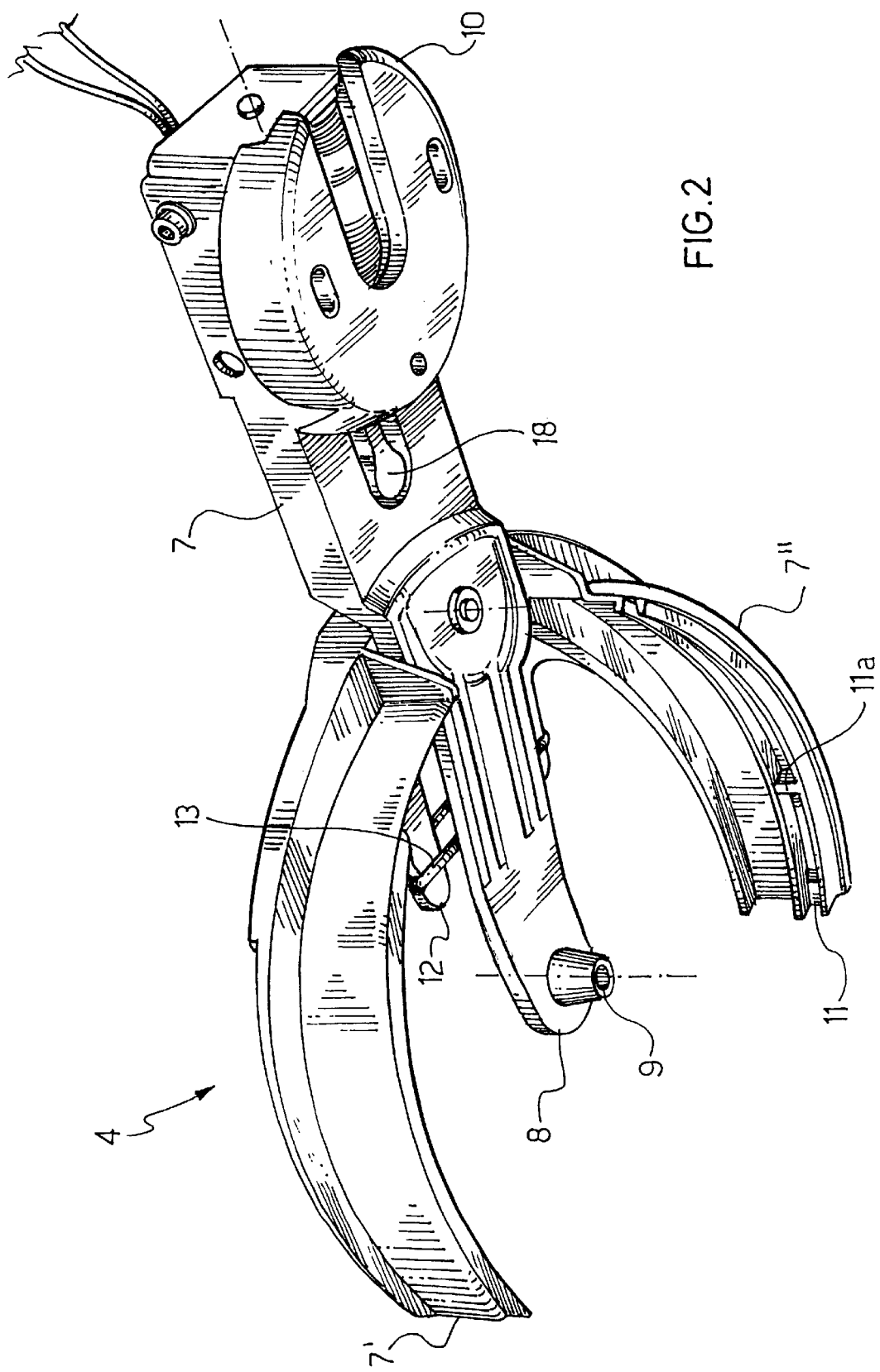
FIG. 2 is a perspective view of a pincer for loading the rotors according to the present invention.
Figure 3:
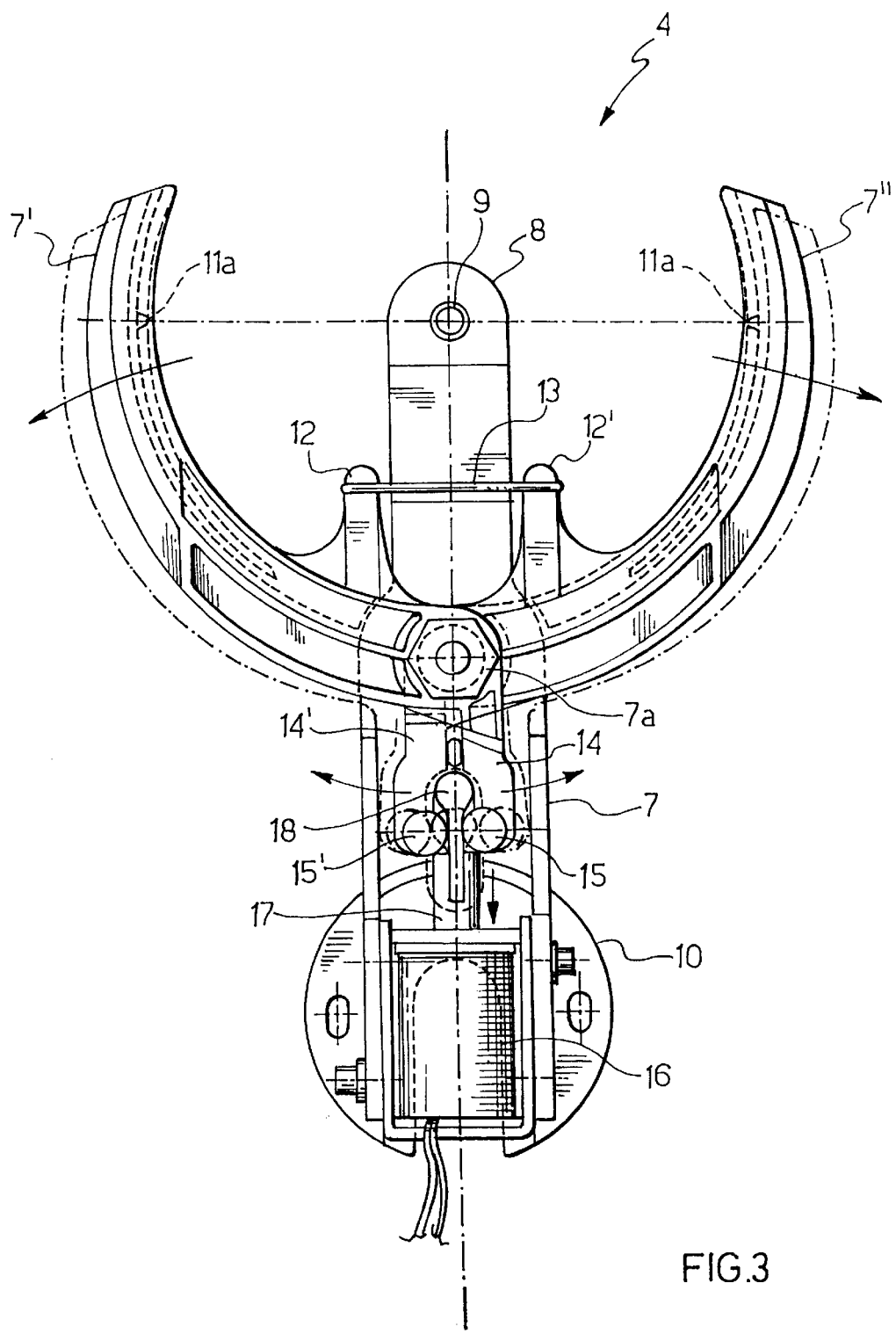
FIG. 3 is a partially-sectioned plan view of the pincer of FIG. 2.

With reference to FIGS. 2 and 3, the pincer 4 comprises an arm 7 and two semicircular and symmetrical claws 7', 7". The claws 7', 7" are supported movably and jointly on the arm 7 by means of a hinge 7a.

The arm 7 comprises a tongue 8 which projects towards the centre of symmetry of the claws 7', 7". At this centre of symmetry, the tongue 8 has a downwardly-projecting finger 9 the function of which will become clear from the following description.

The end of the arm 7 remote from the tongue 8 comprises means 10 for engagement on an actuator (not shown in the drawing) which provides for the movement of the pincer 4 from the region in which the rotors are picked up to the analysis region, as well as for a vertical movement thereof to enable the rotor to be engaged and released.

Each claw 7', 7" comprises a groove 11 for engaging the edges of the rotor 3. On each claw 7', 7", there is a tooth 11a, the teeth 11a preferably being in symmetrical positions within the grooves 11. The teeth 11 a are preferably substantially wedge-shaped.

In the vicinity of their articulation point, the claws 7', 7" have hooks 12, 12' which extend towards the centre of symmetry of the claws, parallel to the tongue 8. The hooks 12, 12' hold resilient joining means 13 such as, for example, a rubber band (shown) or a spring (not shown).

The claws 7', 7" further comprise elements 14, 14' also projecting in the vicinity of the articulation point but in the opposite direction to the hooks 12, 12'. These projecting elements are arranged in a manner such as to be crossed, so that the element 14 projecting from the left-hand claw 7' is disposed on the right-hand side of the element 14' projecting from the right-hand claw 7". The projecting elements 14, 14' also have bulbous ends 15, 15'.

In the vicinity of the engagement means 10 but on the opposite side thereto, the arm 7 supports an electromagnet 16 connected to a current generator (not shown in the drawing). An actuator element 17 terminating in a drop-shaped end 18 is connected to the electromagnet 16. In the rest condition, the drop-shaped end 18 is disposed in the space between the projecting elements 14, 14', as shown in FIG. 3.

Figure 4:
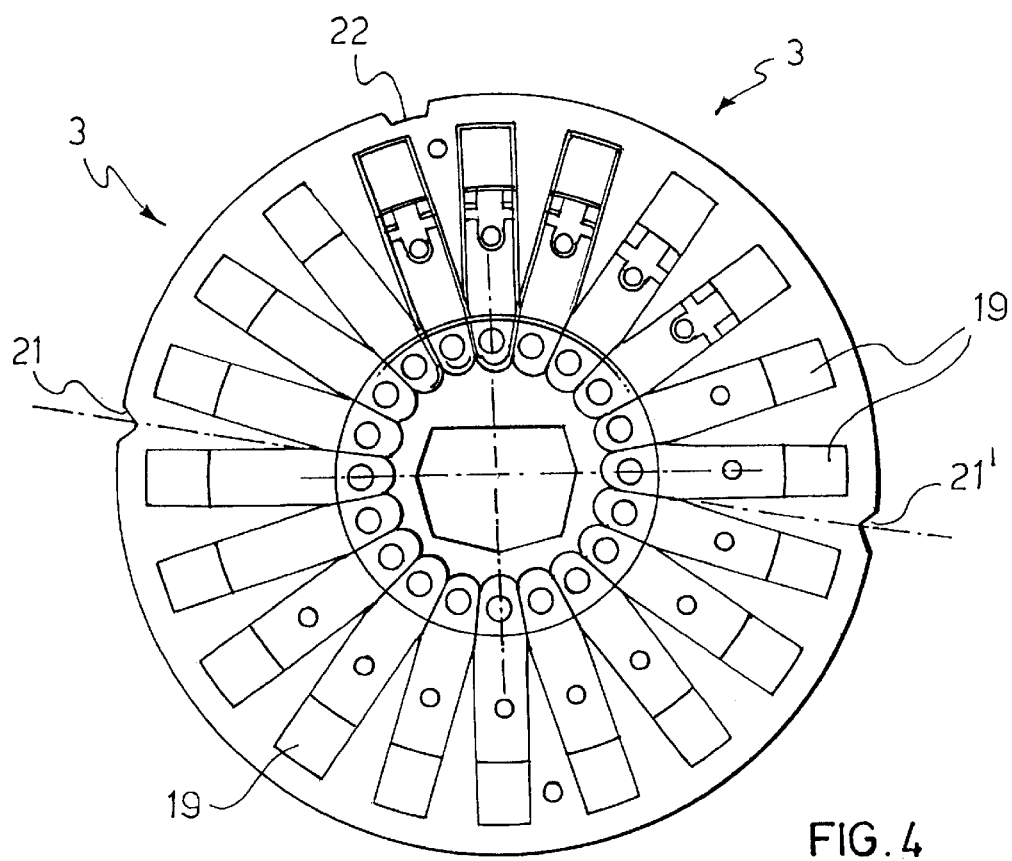
FIG. 4 is a plan view of the rotor of the present invention.

With reference to FIG. 4, the rotor 3 is disk-shaped and is generally made of plastics material. Cuvettes 19 for holding the samples to be analyzed and the reagents are supported radially on its lower surface.

The rotor 3 comprises a central hole 20 for engaging the hub of the analysis apparatus. The central hole 20 may have various shapes. It is preferably polygonal, as shown in the drawing, to ensure the correct angular positioning of the rotor on the hub.

A first notch 21 and a second notch 21' are formed on the peripheral edge of the rotor 3, and are generally (but not necessarily) disposed at the ends of a diameter of the rotor 3. These notches are intended to be engaged by the teeth 11a of the pincer 4 to ensure the correct angular positioning of the rotor on the pincer and consequently in the analysis unit. The shape of these notches substantially corresponds to that of the teeth 11a and is thus preferably V-shaped. The V-shaped notches 21, 21' also advantageously have one side which is more inclined than the other to the bisector of the angle formed thereby so as to constitute a type of lead-in for the teeth 11a during the picking-up of the rotor by the pincer 4.

A third notch 22 which may be of various shapes, for example, trapezoidal as in FIG. 4, is also formed on the peripheral edge of the rotor 3. It is essential for this notch 22 to be in an asymmetric position relative to the first two notches 21, 21', that is, for the circle arc included between the first notch 21 and the third notch 22 to have a different length, for example, a shorter length than the circle arc included between the third notch 22 and the second notch 21'.

The hopper 2 is substantially cylindrical and is open at its two ends. The inside diameter of the hopper 2 substantially corresponds to or is slightly greater than that of the rotors 3. The hopper 2 comprises asymmetric means for locating the rotors 3 positively in the hopper. In practice, the inner surface of the hopper 2 has vertical ribs 23, 23' and 24 corresponding in shape, size and position to the notches 21, 21' and 22 formed on the edge of the rotor 3, respectively.

In the lower portion of the hopper there is a device 25 for separating the rotors. This device comprises two pairs of pincers 26, 26' and 27, 27' disposed one above another on the walls of the hopper. These pincers, which are shaped like arcs of a circle, extend through the walls of the hopper 2 so that, in the closed position, they project towards the interior of the hopper. When the pincers are in the open position, on the other hand, they are retracted inside the walls of the hopper. These pincers are operated by means of an electromagnet device exactly the same as that described above for the pincer 4 (the electromagnet 26a which operates the pincers 26, 26' is shown in broken outline in FIG. 1).

It should be noted that both the hopper 2 and the plate 6 comprise internal electrical resistors (not shown in the drawing) which have the function of thermal conditioning of the rotors at the temperature at which the analysis is performed in the analysis unit 5. This temperature is generally about 37° C. The triangular projections present on the plate 6 also have the purpose of increasing the area of contact between the heated plate and the rotor, improving heat-exchange efficiency.

Moreover, inside the hopper 2 in the region of the two pairs of pincers 26, 26' and 27, 27', there are optical sensors which can detect the presence of a rotor at the level both of the lower pair of pincers 27, 27' and of the upper pair of pincers 26, 26'. This information is then indicated in an appropriate manner, for example, on a control console, to permit human intervention if the hopper is empty or in the event of a malfunction.

Figure 6:
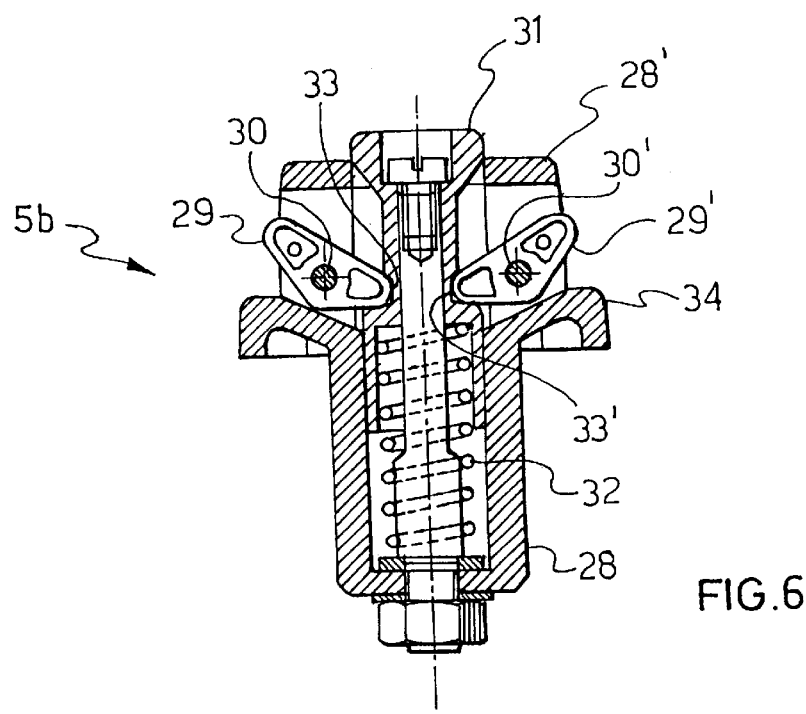
FIG. 6 is a side view showing, in section, the hub on which the rotor is fixed in the analysis apparatus.

With reference to FIG. 6, the hub 5b comprises a hollow body 28 (for fixing to the shaft 5a), the upper portion 28' of which has a cross-section of a shape and size substantially corresponding to those of the central hole 20 in the rotor 3. At the point at which the hollow body 28 is joined to its upper portion 28', there is a projecting annular wall 34 constituting a support point for the rotor 3.

Substantially triangular clips 29, 29' project sideways from the upper portion 28'. These clips are articulated, possibly resiliently, on respective pins 30, 30' so as to be pivotable about the axes extending through these pins. A push-button 31 arranged concentrically inside the hollow body 28 bears on a spring 32. The push-button projects from the top of the upper portion 28' of the hollow body 28. The cylindrical surface of the push-button 31 has recesses 33, 33' in which the inner ends of the clips 29, 29' engage. Clearly, if the push-button 31 is pressed, it will push the inner ends of the clips 29, 29' downwards causing the clips to pivot about the respective pins 30, 30'. The projecting ends of the clips 29, 29' are thus retracted into the upper portion 28' of the hollow body 28. If the push-button 31 is released, it will return to its original position under the effect of the spring 32; the clips 29, 29' will thus be returned to the starting condition in the same manner.

The operation of the rotor-loading device of the present invention will now be described, again with reference to the drawings, particularly FIGS. 5a–5d.

First of all, the rotors 3 are inserted in the hopper 2 by causing the notches 21, 21' 22 to coincide with the respective ribs 23, 23', 24 of the hopper. The separating device 25 will have both pairs of pincers 26, 26' and 27, 27' in the closed position. The stack of rotors 3 thus bears on the upper pair of pincers 26, 26'. At this point, the plate 6 is aligned underneath the hopper 2, and the pincer 4 is arranged in the position for picking up a rotor.

A first and essential advantage of the apparatus of the present invention should be noted. As stated above, the rotor 3 is loaded by causing the notches 21, 21' and the third notch 22 which is disposed in an asymmetric position relative to the other two, to coincide with the ribs 23, 23' 24 of the hopper, respectively. The presence of an asymmetric notch-rib coupling thus clearly excludes the possibility of the rotors being loaded upside down, which would not only invalidate the subsequent analysis but would also cause malfunctioning of the loading device.

Moreover, the correct angular positioning of the ribs 23, 23', 24 determines the final orientation of the rotors 3 on the analysis unit 5 (the alignment of the cuvettes 19 with the optical analysis means).

Figure 5A:
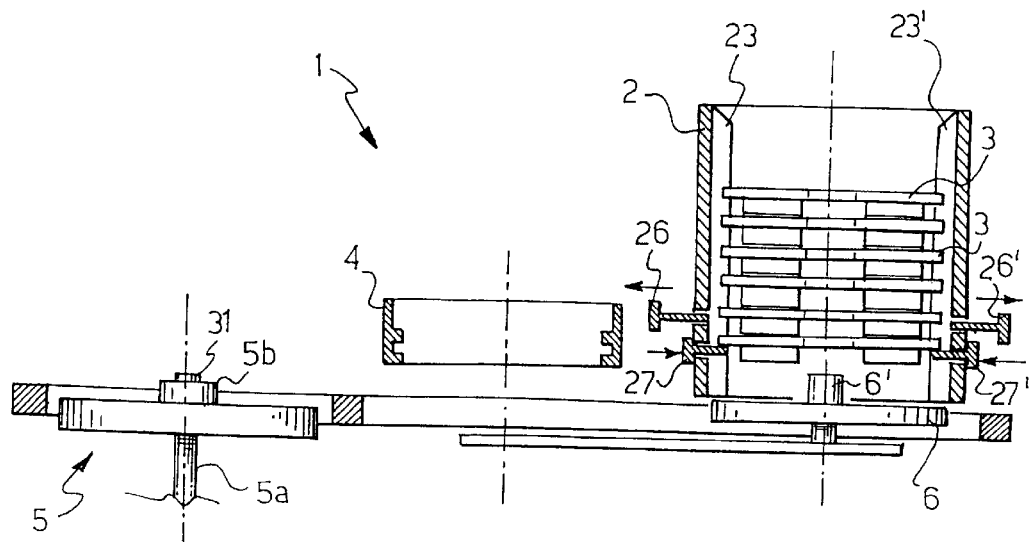
FIGS. 5a–5d show the sequence of steps for loading the rotors on the analysis means, showing the apparatus of FIG. 1 in section.
Figure 5B:
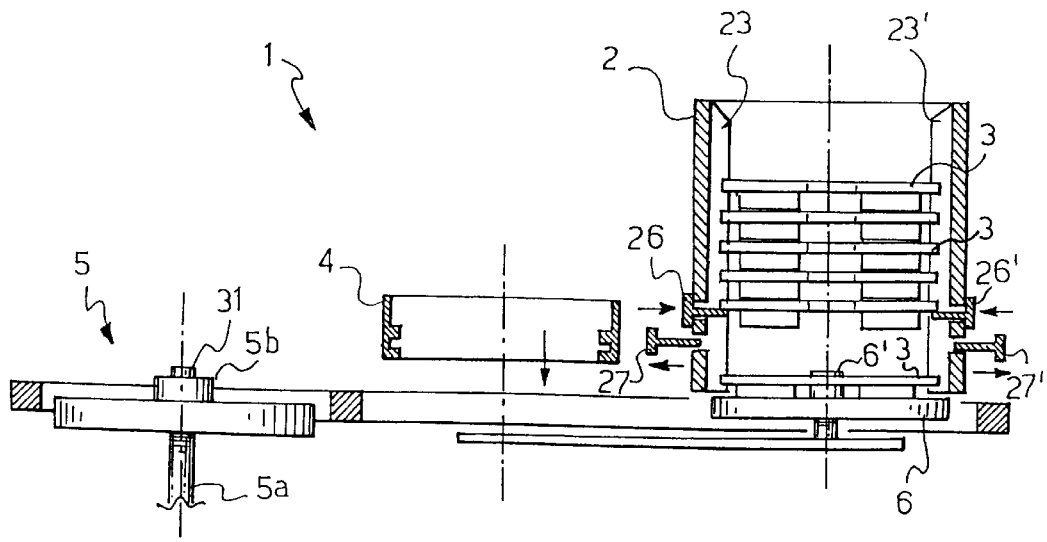

To return to the description of the operation of the apparatus 1, at this point, the upper pair of pincers 26, 26' of the separating device 25 opens, allowing the stack of rotors to fall onto the lower pair of pincers 27,27' as shown in FIG. 5a.

The next step provides for the re-closure of the upper pair of pincers 26, 26' which are interposed between the lowermost rotor 3 and the overlying stack of rotors, separating the lower rotor. As a result of the opening of the lower pair of pincers 27, 27', the lower rotor falls onto the plate 6 (see FIG. 5b). As stated above, the lower surface of the rotor 3, on which the cuvettes 19 are disposed, engages the triangular raised portions projecting from the plate 6, which are arranged in the triangular spaces between one cuvette and another. The correct angular orientation of the rotors is thus maintained.

Figure 5C:
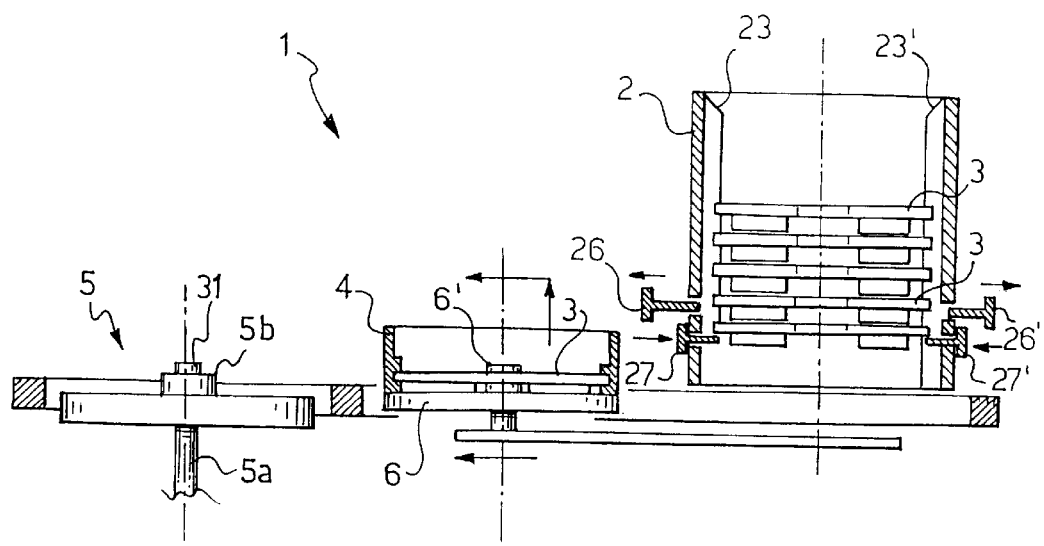
Figure 5D:
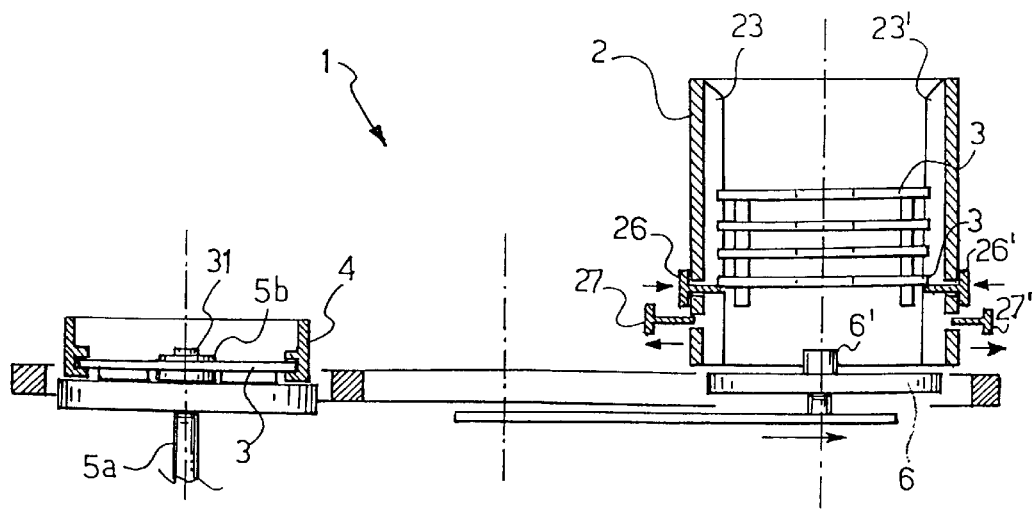

At this point, the plate 6 is translated by the actuator (not shown in the drawings) to the pick-up position of the pincer 4 (see FIG. 5c). At the same time, the lower pair of pincers 27, 27' of the hopper 2 is closed, re-establishing the starting condition.

The pincer 4, the claws 7', 7" of which are open at this point, is moved vertically downwards by the respective actuator so as to place the grooves 11 in a position coplanar with the rotor 3. The claws 7', 7" then close, engaging the outer edge of the rotor. In particular, the teeth 11a engage the notches 21 and 21' of the rotor; the correct angular orientation of the rotor 3 is thus also maintained during its transportation onto the hub 5b of the analysis unit 5.

The pincer 4 is then moved vertically upwards, disengaging the rotor from the plate 6, and is then rotated to the region of the analysis unit 5. At this point, the pincer 4 performs a vertical downward movement. The central hole 20 of the rotor 3 starts to engage the hub 5b. At the same time, the finger 9 disposed on the tongue 8 of the pincer 4 presses the push-button 31 of the hub 5b, causing the clips 29, 29' to be retracted into the upper portion 28' of the hollow body 28. The vertical movement of the pincer 4 is then completed until the lower surface of the rotor 3 engages the projecting wall 34 of the hub 5b. The claws 7', 7" of the pincer 4 open, releasing the rotor 3 and the pincer is then returned to the rotor pick-up position. At the moment when the pincer 4 is raised, the finger 9 stops exerting its pressure on the push-button 31 and the clips 29, 29' consequently return to the starting position, pressing against the edges of the central hole 20 of the rotor 3. This ensures that the angular orientation of the rotor is also constantly correct during the analysis process, during which the rotor is rotated at high speed.

At the moment when the pincer 4 has reached the rotor pick-up position again, the rotor-loading cycle can recommence.

The mechanism for opening and closing the claws of the pincer 4 is as follows. The actuator element 17 is retracted in the direction of the arrow of FIG. 3 by the effect of the electromagnet 16. The drop-shaped end 18 of this actuator element 17 thus acts on the bulbous ends 15, 15' of the projecting elements 14, 14', causing them to move apart. The claws 7', 7" thus open. When the electromagnet 16 returns the actuator element 17 to its initial position, the resilient joining means 13 of the hooks 12, 12' return the claws 7', 7" to the closed position.

The rotor-loading cycle described above, as well as the subsequent analytical process, are generally performed by an operating and control unit (not shown in the drawings) of known type.

The photometric analysis apparatus of the present invention thus has the advantage of enabling the process to be performed automatically, maximizing the productivity of the apparatus. At the same time, the particular characteristic of the provision of at least three notches arranged asymmetrically on the edge of the rotor and complementary to the ribs of the hopper 2, as well as the presence of the triangular raised portions projecting from the plate 6 and of the teeth 11a on the pincer 4, ensure considerable precision in the positioning of the rotor relative to the optical analysis means, which is essential in achieving correct analysis.

Clearly, the embodiment described is only one particular embodiment of the photometric analysis apparatus of the present invention to which an expert in the art may apply any modifications necessary to adapt it to particular applications without, however, departing from the scope of protection of the present invention.

In particular, the notches 21, 21' formed in the edge of the rotor may have shapes other than the substantially triangular shape shown in the drawings. For example, they could be half-moon-shaped or trapezoidal. Naturally, the respective ribs 23, 23' of the hopper 2 and the teeth 11a of the pincer 4 would also have to be modified correspondingly.

The third notch 22 of the rotor may also have a shape other than that shown in the drawing. For example, it could have the same shape as the other two notches 21, 21'.

In this case, the rib 24 of the hopper would have to be modified correspondingly.

The number of notches 21, 21' (and correspondingly of teeth 11a) is not necessarily limited to two and it is also possible to have more than one notch 22. It is, however, essential that the distribution of the notches on the peripheral edge of the rotor should give rise to an asymmetric configuration, as explained above.

In a further embodiment of the present invention, only two notches (to which only two complementary ribs in the hopper 2 correspond) are provided on the edge of the rotor 3. These notches must necessarily have different shapes and the circle arc included between them must extend through an angle of less than 180°, so that it is not possible to identify a plane of symmetry perpendicular to the plane of the rotor and extending through its centre. For example, it is possible to form on the rotor 3 only one of the two V-shaped notches 21, 21' and the trapezoidal notch 22. It will thus still be possible to position the rotors correctly inside the hopper 2. In this embodiment of the present invention, the pincer 4 will also have to be modified by the elimination of one of the two teeth 11a and possibly by the provision of a tooth complementary to the notch 22 of the rotor, on one of the two claws.

For the purposes of the present invention, it is thus essential for the rotor to have at least two asymmetric locating notches having shapes and positions such that it is not possible to identify a plane of symmetry which is perpendicular to the plane in which the rotor lies and which extends through the centre thereof. The same number of complementary ribs disposed inside the hopper 2 will correspond to these notches.

According to further variants of the present invention, the central hole 20 of the rotor may have shapes other than the polygonal shape shown in the drawing. For example, it may have a D-shaped profile or any other profile in which at least one side is straight. In this case, the upper portion 28' of the hub must also be shaped in a corresponding manner.

The rotor 3 described above can also clearly be used on any known photometric analysis apparatus since the notches formed on its edge do not interfere in any way with the performance of the analysis on conventional analysis apparatus.

Moreover, the rotor 3 described and claimed can advantageously also be used on manually-loaded analysis apparatus in which a container is generally provided for the thermal conditioning of the rotors, the rotors being taken from the container manually in order for the analysis to be performed. In this case, the thermal conditioning container will have to be modified suitably by the formation therein of a seat for housing the rotors, in which at least two ribs of different shapes, for example, one of the ribs 23, 23' and the rib 24 will be reproduced. The rotor 3 in turn will have at least two notches, for example, one of the two notches 21, 21' and the notch 22. As explained above, if the rotor has only two notches, they should be of different shapes and should not lie at the ends of a diameter of the rotor. The advantage of this embodiment is that the rotors are positioned correctly in the thermal conditioning container. When the operator-picks them up in order to place them on the analysis unit, he will therefore find them already correctly oriented. The possibility of loading errors is thus eliminated.

What is claimed is:

1. A rotor for photometric analysis, comprising:
a disc comprising a plurality of cuvettes, and at least a first notch positioned on the periphery of said disc, said first notch being V-shaped, wherein one side of the V-shape is more inclined than the other side of the V-shape, thereby providing a lead-in for a pincer to move the rotor from one position to another position.

2. The rotor according to claim 1, further comprising a central hole comprising at least one straight side.

3. The rotor according to claim 2, wherein the central hole is polygonal.

4. The rotor of claim 1 further comprising a second notch.

5. The rotor according to claim 4, wherein the notches are of different shapes and the circle arc included between the two notches extend through an angle of less than 180°.

6. The rotor according to claim 4, wherein the first and second notches are disposed at the ends of a diameter of the rotor.

7. The rotor according to claim 4, further comprising a third notch, the third notch being arranged in an asymmetric position relative to the first and second notches so that a circle arc included between the first notch and the third notch has a length different from that of circle arc included between the third notch and the second notch.

8. The rotor according to claim 7, wherein at least one notch is substantially trapezoidal.

* * * * *